United States Patent
Yu

(10) Patent No.: US 7,555,083 B2
(45) Date of Patent: Jun. 30, 2009

(54) SYNCHRONIZING CIRCUIT FOR STABLY GENERATING AN OUTPUT SIGNAL

(75) Inventor: Bum-Seok Yu, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 721 days.

(21) Appl. No.: 10/968,507

(22) Filed: Oct. 19, 2004

(65) Prior Publication Data
US 2005/0147195 A1    Jul. 7, 2005

(30) Foreign Application Priority Data
Jan. 7, 2004    (KR)   ............ 10-2004-0000974

(51) Int. Cl.
*H04L 7/00*    (2006.01)
(52) U.S. Cl. ......................................... 375/354
(58) Field of Classification Search ................. 375/354
See application file for complete search history.

(56) References Cited

U.S. PATENT DOCUMENTS 5,867,409 A * 2/1999 Nozuyama ............ 708/252
2002/0067785 A1* 6/2002 Tanahashi ............ 375/354

\* cited by examiner

*Primary Examiner*—David C Payne
*Assistant Examiner*—Nader Bolourchi
(74) *Attorney, Agent, or Firm*—F. Chau & Associates, LLC

(57) ABSTRACT

The present invention relates to a synchronizing circuit for stably generating an output signal irrespective of the frequency difference of clocks. According to the present invention, the synchronizing circuit receives an input signal synchronized with a first clock and then stores a state of the input signal so that the input signal is synchronized with a transition of a second clock. then, the synchronizing circuit generates an output signal synchronized with the transition of the second clock. In addition, an input signal synchronized with the first clock becomes synchronized with the second clock having a lower frequency than the first clock.

17 Claims, 8 Drawing Sheets

| $S_1$ | Input | $S_0$ |
|---|---|---|
| 0 | 0 | $S_2$ |
| 0 | 1 | 1 |
| 1 | 0 | 0 |
| 1 | 1 | 1 |

SYNCHRONIZING CIRCUIT FOR STABLY GENERATING AN OUTPUT SIGNAL

CROSS-REFERENCE TO RELATED APPLICATION

This U.S. non-provisional patent application claims priority under 35 U.S.C. § 119 to Korean Patent Application 2004-00974 filed on Jan. 7, 2004, the entire contents of which are hereby incorporated by reference.

BACKGROUND OF THE INVENTION

Circuits requiring different clocks may be used, for example, in a synchronous system. When a plurality of clocks are used in the system, there is typically a request to synchronize input signals with the plurality of clocks to stably operate the system.

In this case, synchronization means that input signals are inputted to stably generate output signals that are synchronized with transitions of one or more clocks. A synchronization circuit is typically referred to as a circuit capable of stably synchronizing input signals with a plurality of clocks.

Assuming that a cycle of an input signal is T1, and a cycle of a clock is T2, in a flip-flop, the following relations are obtained. If T1>T2, the flip-flop receives the input signal to stably generate an output signal synchronized with a transition of the clock. To the contrary, if T1<T2, the input signal is not synchronized with the transition of the clock, so it may disappear.

In a case where an input signal is a pulse signal with a long cycle synchronized with a transition of a first clock, the input signal may become synchronized with a transition of a second clock with a short cycle, which also has a frequency higher than the first clock, thus generating an output signal. Therefore, the input signal can be prevented from disappearing. This is, because the cycle of the input signal is longer than that of the second clock. In other words, the input signal meets the transition of the second clock (e.g., a low-high transition) more than once when it is at a high level.

However, when the input signal is a pulse signal with a short cycle synchronized with the transition of the first clock, but not synchronized with the transition of the second clock with a long cycle and a low frequency, the input signal may disappear. This is, because the input signal may not meet the transition of the second clock more than once when it is at a high level.

Accordingly, a synchronization circuit for stably generating an output signal by synchronizing an input signal with the transition of the first clock and the transition of the second clock is desired.

SUMMARY OF THE INVENTION

The present invention is directed to a synchronizing circuit for stably generating an output signal by synchronizing an input signal with a transition of a first clock to a transition of a second clock having a lower frequency than the first clock.

The synchronizing circuit comprises: an input signal synchronized with a transition of a first clock; an input device for generating a first signal in response to the input signal, for synchronizing the first signal with a transition of a second clock, and for initializing the first signal in response to a second signal; a first device for generating a third signal in synchronization with the transition of the second clock in response to the first signal; a second device for generating the second signal in synchronization with the transition of the second clock in response to the third signal; and a pulse generator for generating an output signal in response to the second and third signals. The first clock has a higher frequency than the second clock.

The input device comprises: an input signal processor for generating a set signal in response to the input signal, for generating a reset signal in response to the second signal, and for generating a maintenance signal in response to the first signal fed back to the input signal processor; and a third device for generating the first signal in synchronization with the transition of the first clock in response to the set signal, for synchronizing the first signal with the transition of the second clock in response to the maintenance signal, and for initializing the first signal in synchronization with the transition of the first clock in response to the reset signal.

The input signal processor comprises a first multiplexer for selecting data "0" according to the second signal to generate the reset signal; and a second multiplexer for selecting data "1" according to the input signal to generate the set signal.

The input signal processor generates the set signal when the input signal and the second signal are inputted simultaneously. The input signal processor receives the fed-back first signal to generate the maintenance signal when the input signal and the second signal are not inputted.

Another aspect of the present invention is to provide a synchronizing circuit comprising: an input signal synchronized with a transition of a first clock; a first device for generating a second signal in response to a first signal fed-back to the first device in synchronization with a transition of the first clock and for outputting the first signal; an input device for generating a third signal in response to the input signal, for synchronizing the third signal with a transition of a second clock, and for initializing the third signal in response to the second signal; a second device for generating a fourth signal in synchronization with the transition of the second clock in response to the second signal; a third device for generating the first signal in synchronization with the transition of the second clock in response to the fourth signal; and a pulse generator for generating an output signal in response to the third and fourth signals. The first clock has a higher frequency than the second clock.

The input device comprises an input signal processor for generating a set signal in response to the input signal, for generating a reset signal in response to the second signal, and for generating a maintenance signal in response to the third signal fed-back to the input signal processor; and a fourth device for generating the third signal in synchronization with the transition of the first clock in response to the set signal, for synchronizing the third signal with the transition of the second clock in response to the maintenance signal, and for initializing the second signal in synchronization with the transition of the first clock in response to the reset signal.

The input device comprises a first multiplexer for selecting data "0" according to the second signal to generate the reset signal; and a second multiplexer for selecting data "1" according to the input signal to generate the set signal.

The input signal processor generates the set signal when the input signal and the second signal are inputted simultaneously. The input signal processor generates the maintenance signal in response to the second signal fed-back to the input signal processor when the input signal and the second signal are not inputted. The first to fourth devices are flip-flops.

Still another aspect of the present invention is to provide a synchronizing circuit comprising: an input signal synchronized with a transition of a first clock; a plurality of first flip-flops for generating a second signal in response to a first signal fed-back to the plurality of first flip-flops in synchronization with a transition of the first clock, wherein at least two of the plurality of flip-flops are connected in series; an input device for generating a third signal in response to the input signal, for synchronizing the third signal with a transition of a second clock, and for initializing the third signal in response to the second signal; a second flip-flop for generating a fourth signal in synchronization with the transition of the second clock in response to the third signal; a plurality of third flip-flops for generating the first signal in synchronization with the transition of the second clock in response to the fourth signal, wherein at least two of the plurality of third flip-flops are connected in series; and a pulse generator for generating an output signal in response to the fourth signal, and the first signal generated by the plurality of third flip-flops. The first clock has a higher frequency than the second clock.

The input device comprises an input signal processor for generating a set signal in response to the input signal, for outputting the reset signal in response to the first signal, and for generating a maintenance signal in response to the third signal fed-back to the input signal processor; and a fourth flip-flop for generating a third signal in synchronization with the transition of the first clock in response to the set signal, for synchronizing the third signal with the transition of the second clock in response to the maintenance signal, and for initializing the third signal in synchronization with the transition of the first clock in response to the reset signal.

The input signal processor comprises a first multiplexer for selecting data "0" according to the second signal to generate the reset signal; and a second multiplexer for selecting data "1" according to the input signal to generate the set signal.

The input signal processor generates the set signal when the input signal and the second signal are inputted simultaneously. The input signal processor generates the maintenance signal in response to the third signal fed-back to the input signal processor when the input signal and the second signal are not inputted. The first to fourth flip-flops are D-flip-flops.

BRIEF DESCRIPTION OF THE DRAWINGS

The above and other features of the present invention will become more apparent by describing in detail exemplary embodiments thereof with reference to the attached drawings, in which.

DETAILED DESCRIPTION OF PREFERRED EMBODIMENTS

Figure 1:
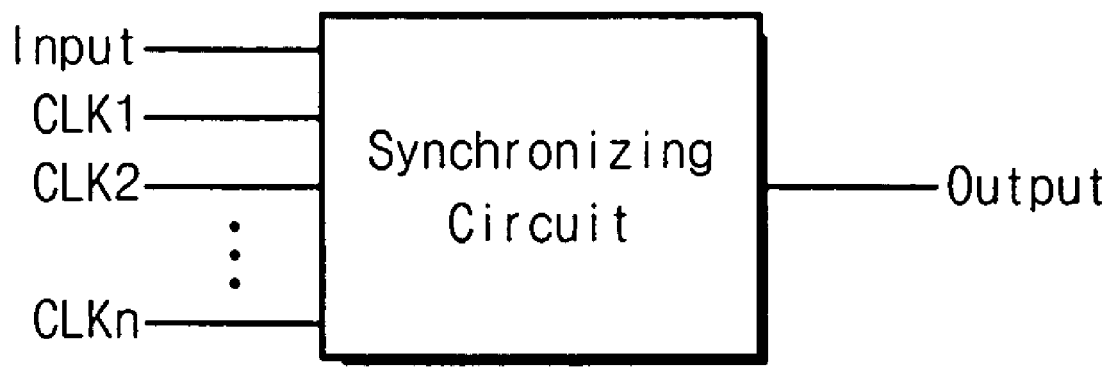
FIG. 1 is a concept diagram of a synchronizing circuit requiring a plurality of clocks.

FIG. 1 is a concept diagram of a synchronizing circuit requiring a plurality of clocks CLK1 to CLKn. The synchronizing circuit includes the plurality of clocks CLK1 to CLKn for operating internal circuits (not shown). Each of the plurality of clocks CLK1 to CLKn has a different frequency. The synchronizing circuit generates an output signal stably synchronized with the plurality of clocks CLK1 to CLKn irrespective of the different frequencies of the plurality of clocks CLK1 to CLKn.

Figure 2:
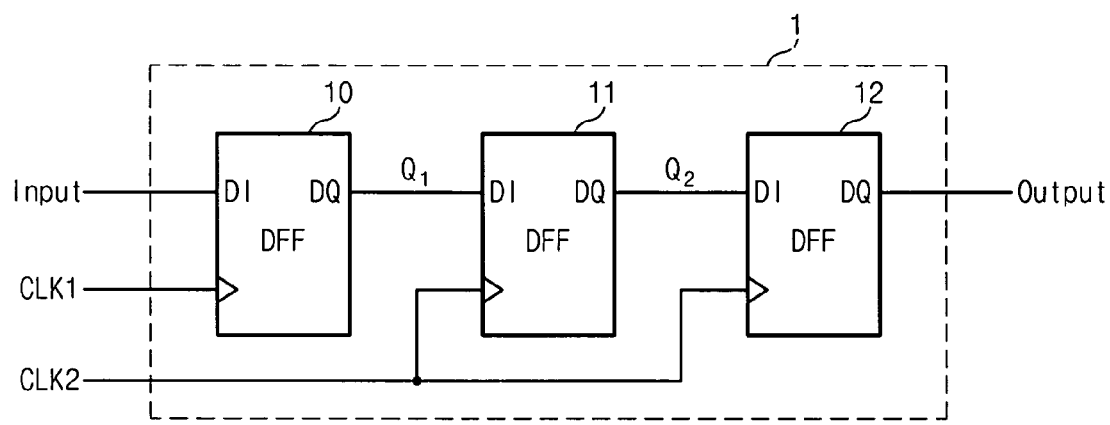
FIG. 2 is a circuit diagram of an embodiment of the synchronizing circuit of FIG. 1.

FIG. 2 shows an embodiment of the synchronizing circuit of FIG. 1 constituted with three flip-flops. A synchronizing circuit 1 comprises a flip-flop 10 synchronized with a first clock CLK1 and two flip-flops 11 and 12 synchronized with a second clock CLK2.

Figure 3:
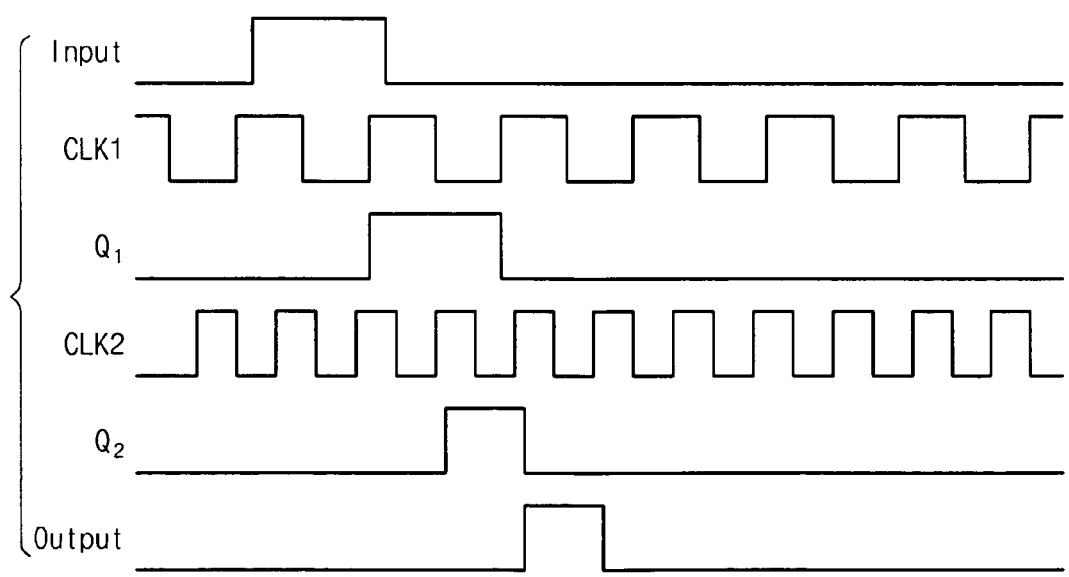
FIG. 3 is a timing diagram illustrating when a second clock has a higher frequency than a first clock in the synchronizing circuit of FIG. 2.

FIG. 3 is a timing diagram illustrating when the second clock CLK2 has a higher frequency than the first clock CLK1 in the synchronizing circuit 1. Referring to FIG. 3, an operation of the synchronizing circuit 1 is described as follows.

As shown in FIG. 3, an input signal Input is synchronized with the first clock CLK1. The first flip-flop 10 receives the input signal Input to generate a first signal Q1 synchronized with a low-high transition of the first clock CLK1. If the input signal Input is high, the first signal Q1 is synchronized with the low-high transition of the first clock CLK1 so that it is changed from low to high. In addition, if the input signal Input is low, the first signal Q1 is synchronized with a next low-high transition of the first clock CLK1 so that it is changed from high to low.

The second flip-flop 11 receives the first signal Q1 to generate a second signal Q2, which becomes synchronized with a low-high transition of the second clock CLK2. If the first signal Q1 is high, the second signal Q2 is synchronized with the low-high transition of the second clock CLK2 so that it is changed from low to high. In addition, if the first signal Q1 is low, the second signal Q2 is synchronized with the next low-high transition of the second clock CLK2 so that it is changed from high to low.

The third flip-flop 12 receives the second signal Q2 to generate an output signal Output synchronized with the low-high transition of the second clock CLK2. The third flip-flop 12 is added to stably synchronize the first signal Q1 with the second clock CLK2. The reason for this is that the second signal Q2 may generate an unwanted signal (hereinafter referred to as "glitch") depending on a setup or hold condition. The output signal Output is also synchronized with the first clock CLK1 as well as the second clock CLK2 because of the addition of the third flip-flop 12.

As further shown in FIG. 3, when a signal having a long cycle synchronized with a transition of a clock having a low frequency becomes synchronized with a transition of a clock having a high frequency, the signal does not disappear. The reason for this is that a cycle of the signal is longer than that of the clock.

Figure 4:
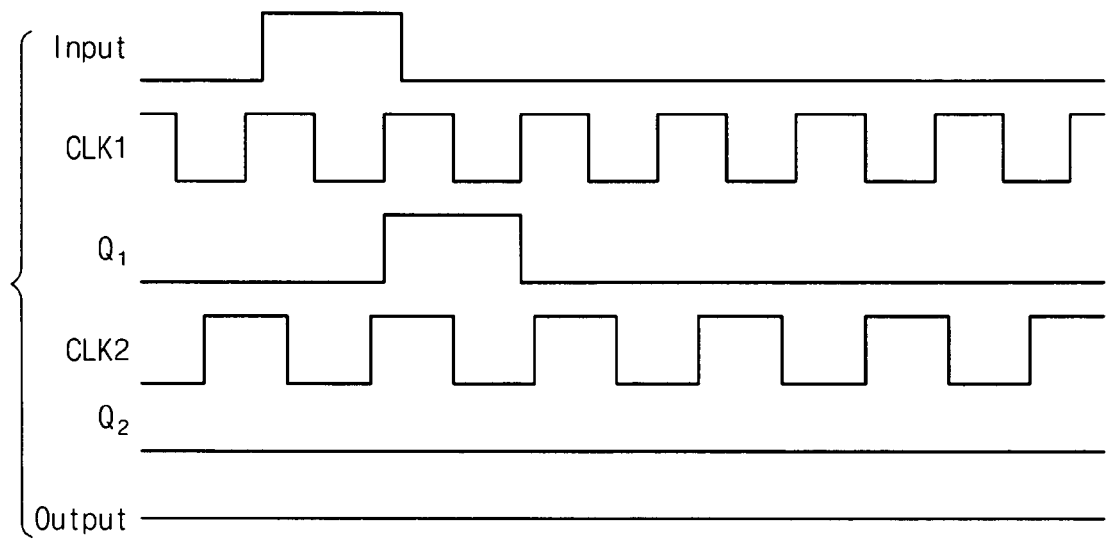
FIG. 4 is a timing diagram illustrating when the first clock has a higher frequency than the second clock in the synchronizing circuit of FIG. 2.

FIG. 4 is a timing diagram illustrating when the first clock CLK1 has a higher frequency than the second clock CLK2 in the synchronizing circuit 1. An operation of the synchronizing circuit 1 according to the timing diagram of FIG. 4 is similar to that as described for FIG. 3 and is thus omitted.

Referring to FIG. 4, there is a phenomenon that the second signal Q2 disappears. The reason for this is that the first signal Q1 having a short pulse width by being synchronized with the first clock CLK1 having a high frequency becomes synchronized with the second clock CLK2 having long cycle. In other words, as shown in FIG. 4, while the first signal Q1 is high, there is a possibility that the first signal Q1 and the low-high transition of the second clock CLK2 do not meet. In order to prevent the phenomenon, there is a request to increase the pulse width of the first signal Q1 rather than increasing a cycle of the second clock CLK2.

Figure 5:
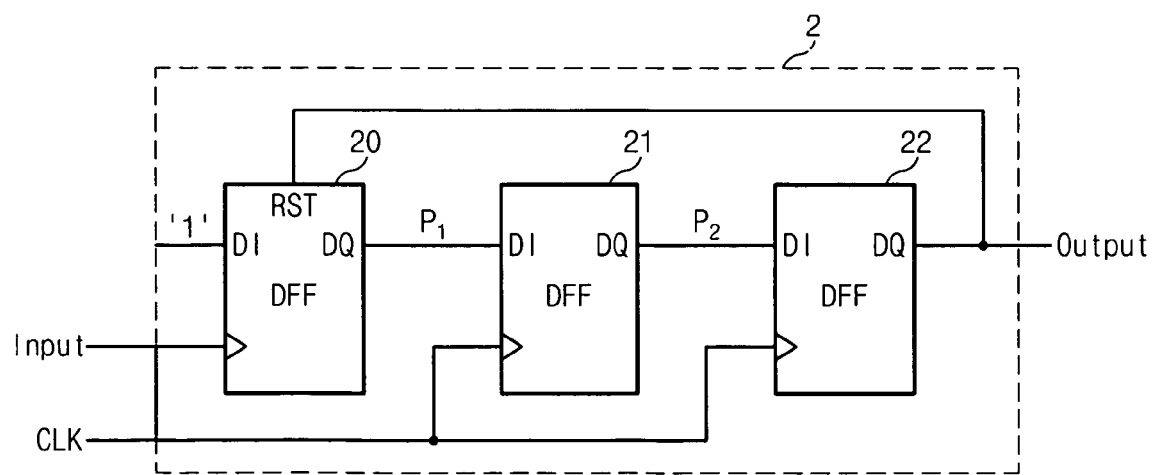
FIG. 5 is a circuit diagram showing another embodiment of the synchronizing circuit of FIG. 1.

FIG. 5 is a circuit diagram showing another embodiment of the synchronizing circuit of FIG. 1. Referring to FIG. 5, a synchronizing circuit 2 is constituted of three flip-flops 20, 21 and 22. The synchronizing circuit 2 comprises a first flip-flop 20 synchronized with, e.g., a first clock CLK1 and second and third flip-flops 21 and 22 synchronized with, e.g., a second clock CLK2.

The synchronizing circuit 2 receives data "1". The synchronizing circuit 2 receives data "1" to be synchronized with a low-high transition of an input signal Input, and then outputs the data. In addition, the synchronizing circuit 2 includes a means such as a reset pin RST in the first flip flop 20 for initializing the first flip-flop 20 in response to an output signal Output.

Figure 6:
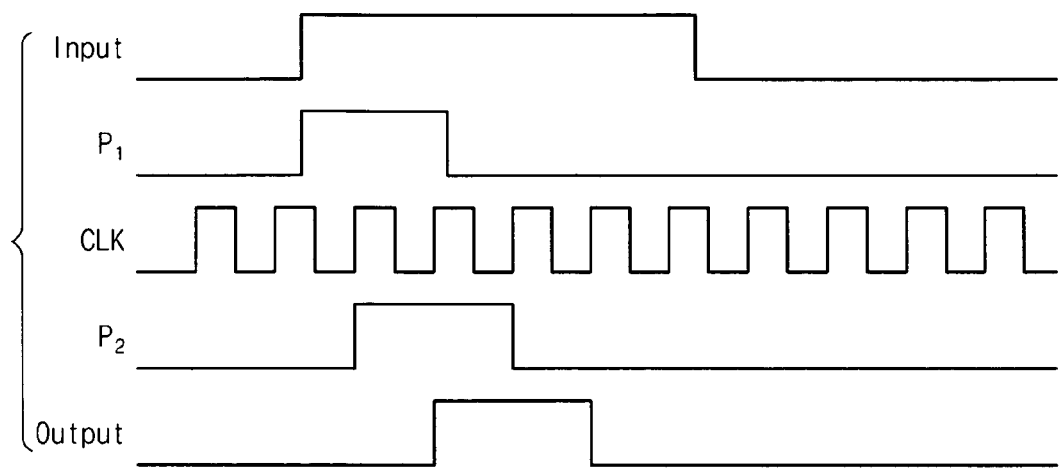
FIG. 6 is a timing diagram illustrating when a normal input signal is inputted into the synchronizing circuit of FIG. 5.

FIG. 6 is a timing diagram illustrating when a normal input signal is inputted into the synchronizing circuit 2. An operation of the synchronizing circuit 2 will now be described referring to FIG. 6.

The first flip-flop 20 receives data "1". The first flip-flop 20 becomes synchronized with the low-high transition of the input signal Input to generate a first signal P1. The first signal P1 becomes synchronized with the low-high transition of the input signal Input to be changed from low to high.

The second flip-flop 21 receives the first signal P1 to output a second signal P2 synchronized with a low-high transition of a clock CLK. The second signal P2 becomes synchronized with the low-high transition of the clock CLK to be changed from low to high on a condition that the first signal P1 is high. The second signal P2 becomes synchronized with the low-high transition of the clock CLK to be changed from high to low on the condition that the first signal P1 is high.

The third flip-flop 22 receives the second signal P2 to generate an output signal Output synchronized with the low-high transition of the clock CLK. The output signal Output becomes synchronized with the low-high transition of the clock CLK to be changed from low to high on a condition that the second signal P2 is high. The output signal Output becomes synchronized with the low-high transition of the clock CLK to be changed from high to low on the condition that the second signal P2 is high. The third flip-flop 22 is added in order to stably synchronize the first signal P1 with the clock CLK.

The output signal Output is input to the first flip-flop 20. The output signal Output is applied to the reset pin RST of the first flip-flop 20. The first signal P1 is then changed from high to low when the output signal Output is inputted to the first flip-flop 20.

Figure 7:
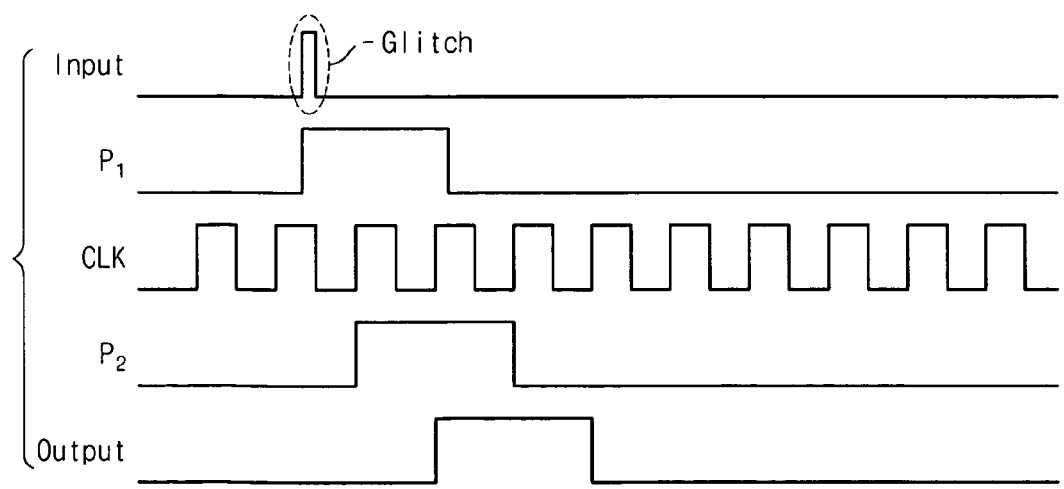
FIG. 7 is a timing diagram illustrating when an abnormal input signal is inputted into the synchronizing circuit of FIG. 5.

FIG. 7 is a timing diagram illustrating when the input signal Input is abnormally inputted into the synchronizing circuit 2. As shown in FIG. 7, if there is a glitch associated with the input signal Input, an unwanted output signal may arise.

As shown in FIG. 7, the first signal P1 is changed from low to high in response to the glitch of the input signal Input. The second signal P2 becomes synchronized with a low-high transition of a clock CLK to be generated. The output signal Output is delayed one cycle of the second signal P2. In another approach, the output signal Output is fed-back to the first flip-flop 20. The first signal P1 is then changed from high to low as the output signal Output is inputted to the first flip-flop 20. Because the output signal Output is generated by inputting the input signal Input with the glitch as shown in FIG. 7, the synchronizing circuit 2 mis-operates.

Figure 8:
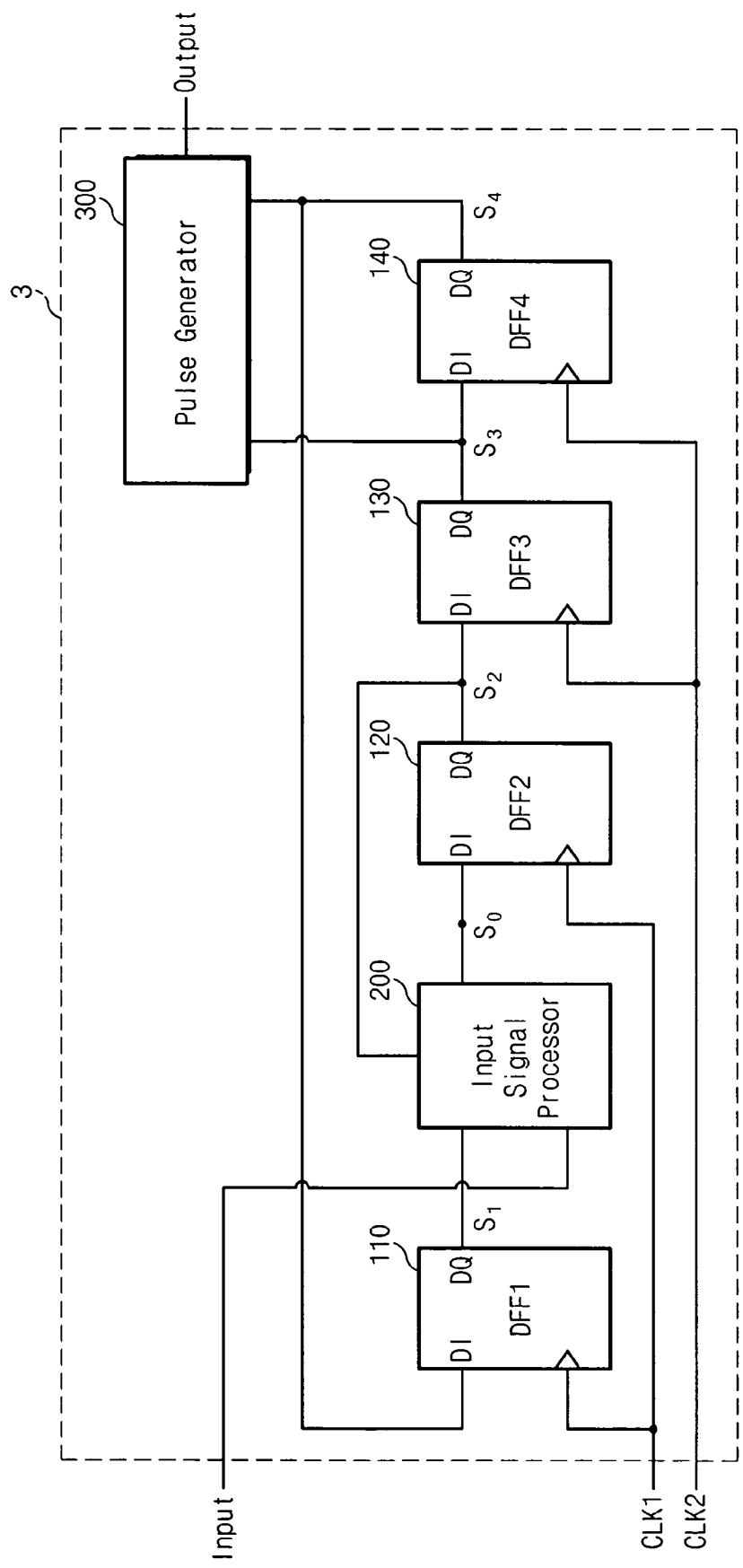
FIG. 8 is a block diagram showing an exemplary embodiment of a synchronizing circuit according to the present invention.

FIG. 8 is a block diagram showing an exemplary embodiment of a synchronizing circuit 3 according to the present invention. As discussed below, the synchronizing circuit 3 stably generates an output signal synchronized with the transition of first and second clocks irrespective of the frequency differences of the first and second clocks as well as a glitch.

As shown in FIG. 8, the synchronizing circuit 3 includes flip-flops 110, 120, 130 and 140, an input signal processor 200 and a pulse generator 300. The synchronizing circuit 3 receives first and second clocks CLK1 and CLK2 having different frequencies and an input signal Input to generate an output signal Output. In this case, the input signal Input is synchronized with the transition of the first clock CLK1.

Referring to FIG. 8, the first and second flip-flops 110 and 120 are synchronized with a first clock CLK1, and the third and fourth flip-flops 130 and 140 are synchronized with a second clock CLK2. In this case, the first clock CLK1 has a higher frequency than the second clock CLK2.

As further shown in FIG. 8, the first flip-flop 110 receives a fourth signal S4 fed-back from the fourth flip-flop 140. The first flip-flop 110 receives the fourth signal S4 to be synchronized with the low-high transition of the first clock CLK1 and then outputs a first signal S1. When the input signal processor 200 receives the first signal S1, it outputs data "0". When the input signal processor 200 receives the input signal, it outputs data "1". When the input signal processor 200 receives the first signal S1 and the input signal Input simultaneously, it outputs the data "1". In addition, the input signal processor 200 outputs the second signal S2 in response to the second signal S2 when the first signal S1 and the input signal Input are not inputted thereto.

Figures 9A, 9B:
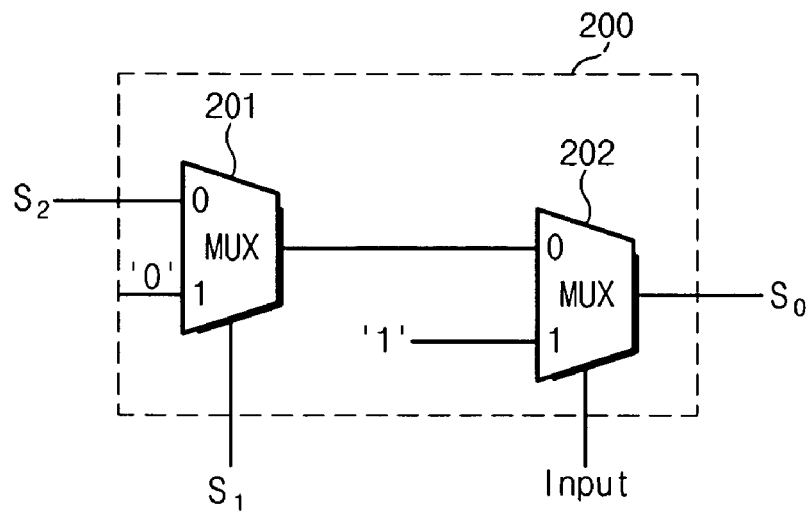
FIG. 9A is a circuit diagram showing an exemplary embodiment of an input signal processor of the synchronizing circuit of FIG. 8.
FIG. 9B is a table showing states of input/output signals of the input signal processor.

FIG. 9A is a circuit diagram showing an exemplary embodiment of the input signal processor 200. The input signal processor 200 is structured by two multiplexers 201 and 202.

The first multiplexer 201 receives the first signal S1 from the first flip-flop 110. The first multiplexer 201 selects data "0" or the second signal S2 fed-back from the second flip-flop 120 according to the first signal S1. When the first signal S1 is high, the data "0" is selected, and to the contrary, when the first signal S1 is low, the second signal S2 is selected.

The second multiplexer 202 selects data "1" or a value outputted from the first multiplexer 210 according to the input signal Input. When the input signal Input is high, the data "1" is selected, and to the contrary, when the input signal Input is low, an outputted value from the first multiplexer 201 is selected.

FIG. 9B is a table showing a signal S0 outputted from the input signal processor 200 according to a state of the first signal S1 or the input signal Input. When the first signal S1 and the input signal Input are low, the input signal processor 200 outputs the second signal S2. When the first signal S1 is low, and the input signal Input is high, the input signal processor 200 outputs data "1". In addition, when the first signal S1 is high, and the input signal Input is low, the input signal processor 200 outputs data "0". When the first signal S1 and the input signal Input are high, the input signal processor 200 outputs data "1".

Referring to FIG. 8 again, the second flip-flop 120 receives a signal S0 outputted from the input signal processor 200. The second flip-flop 120 receives the outputted signal S0 to be synchronized with a low-high transition of the first clock CLK1, and then outputs a second signal S2.

The second flip-flop 120 receives data "0" or data "1" from the input signal processor 200, and it outputs data "0" or "data "1", respectively. In addition, when the second flip-flop 120 receives a fed-back second signal S2, it maintains a state of the original second signal S2.

The second flip-flop 120 stores a variation of the input signal Input. In other words, when the input signal Input is changed from low to high, the second signal S2 becomes synchronized with a low-high transition of the first clock CLK1 to be changed from low to high. The second signal S2 also maintains a high state until the first signal S1 is changed from low to high. As a result, the second signal S2 may be synchronized with the transition of the second clock CLK2 more than once. When the first signal S1 is changed from low to high, the second signal S2 becomes synchronized with the low-high transition of the first clock CLK1 to be changed from high to low.

The third flip-flop 130 receives the second signal S2 from the second flip-flop 120. The third flip-flop 130 receives the second signal S2 to be synchronized with the low-high transition of the second clock CLK2 and then outputs a third signal S3. The second signal S2 is synchronized with respect to the first clock CLK1 but is not synchronized with respect to the second clock CLK2. However, when the second signal S2 maintains a high state until the first signal S1 is changed from low to high, it has longer cycle than the second clock CLK2. Accordingly, because the cycle of the second signal S2 is longer than that of the second clock CLK2, the second signal S2 is not removed from an output terminal of the third flip-flop 130.

The fourth flip-flop 140 receives the third signal S3 from the third flip-flop 130. The fourth flip-flop 140 receives the third signal S3 to be synchronized with the low-high transition of the second clock CLK2 and then outputs a fourth signal S4.

A glitch may occur in the third signal S3 due to a setup or hold condition with respect to the second clock CLK2. Therefore, in order to stably synchronize the third signal S3 with the second clock CLK2, an additional flip-flop is required. The fourth flip-flop 140 is added to stably synchronize the third signal S3.

The pulse generator 300 receives the third and fourth signals S3 and S4 to generate an output signal Output. The pulse generator 300 may generate the output signal Output in a desired wave-shape according to an internal structure of the synchronizing circuit 3.

Figure 10A:
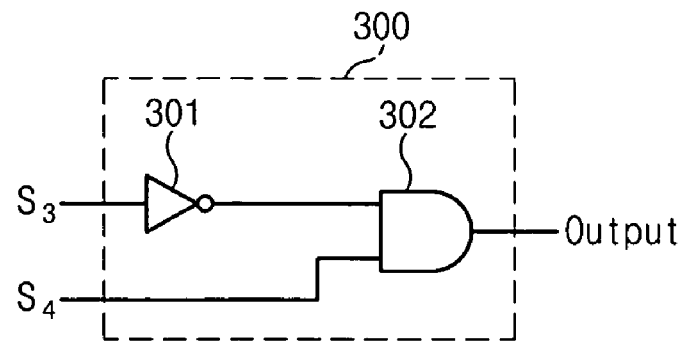
FIG. 10A is a circuit diagram showing an exemplary embodiment of a pulse generator of the synchronizing circuit of FIG. 8.
Figure 10B:
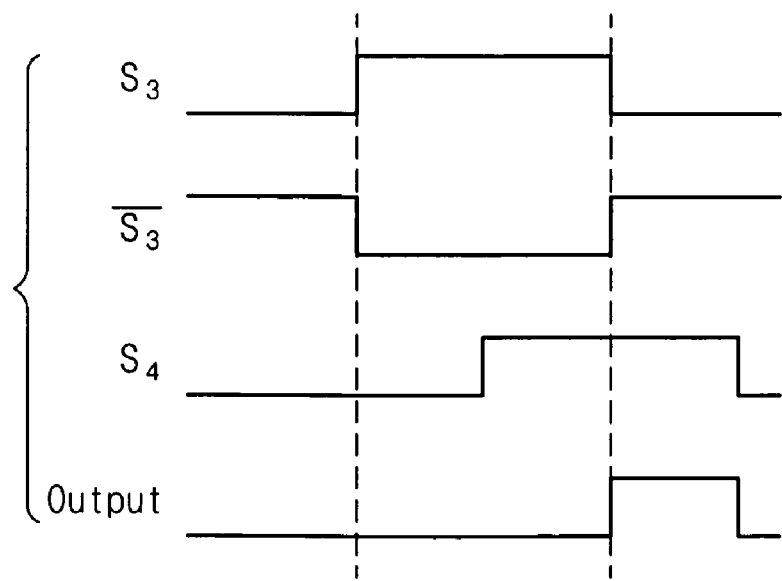
FIG. 10B is a timing diagram showing input/output signals of the pulse generator.

FIG. 10A is a circuit diagram showing an exemplary embodiment of the pulse generator 300. FIG. 10B is a timing diagram of the pulse generator 300. The pulse generator 300 is structured by one inverter 301 and one AND gate 302. The inverter 301 receives the third signal S3 from the third flip-flop 130 to generate a reversed signal/S3. The AND gate 302 receives the reversed signal/S3 and the fourth signal S4. The AND gate 302 generates a pulse Output (e.g., the output signal Output) where the signals/S3 and S4 are high.

Figure 11:
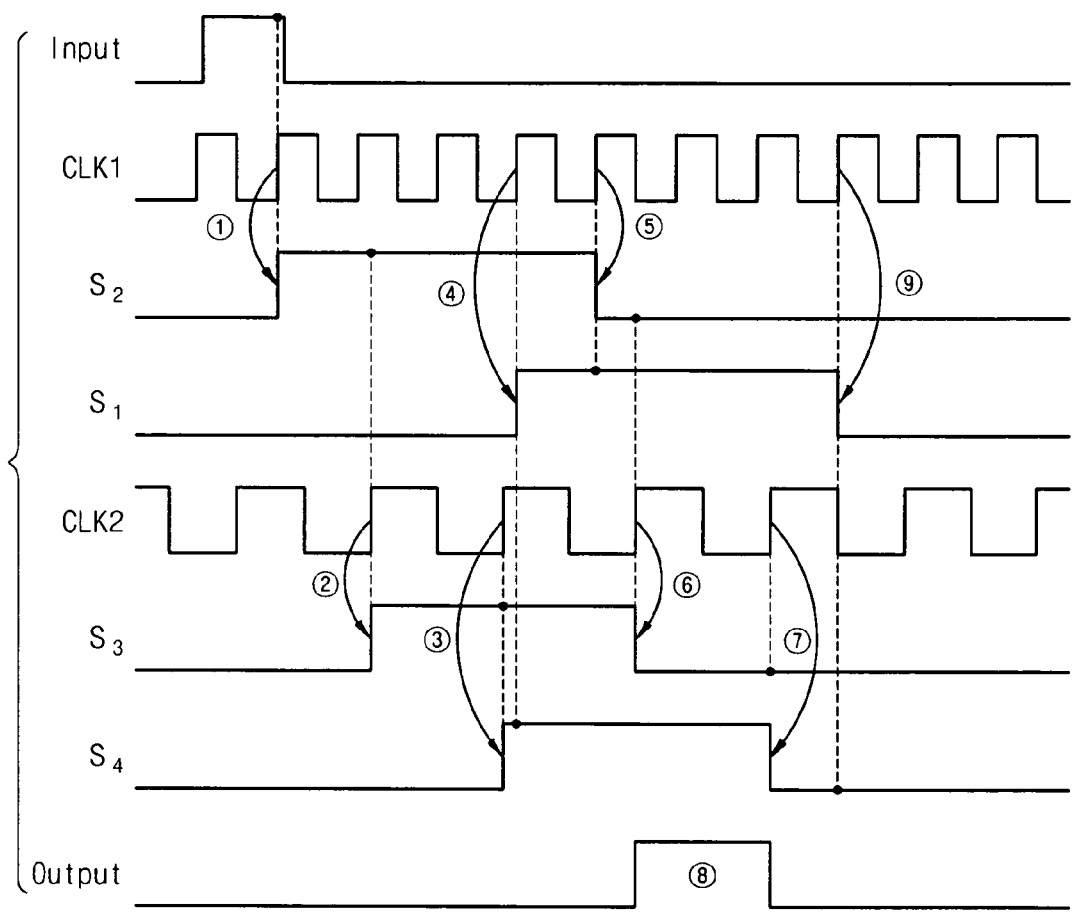
FIG. 11 is a timing diagram of the synchronizing circuit of FIG. 8.

FIG. 11 is a timing diagram of the synchronizing circuit 3. An operation of the synchronizing circuit 3 will be described referring to FIG. 11.

An input signal Input is synchronized with the first clock CLK1. In the first step, the second signal S2 is synchronized with a low-high transition of the first clock CLK1 to be changed from low to high on a condition that the input signal Input is high. The second signal S2 is fed-back to the input signal processor 200. Accordingly, the second signal S2 is synchronized with a next low-high transition of the first clock CLK1 to be changed from high to low on a condition that the input signal Input is low. The second signal S2 is maintained high.

In the second step, the third signal S3 is synchronized with the low-high transition of the second clock CLK2 to be changed from low to high on a condition that the second signal S2 is high.

In the third step, the fourth signal S4 is synchronized with the low-high transition of the second clock CLK2 to be changed from low to high on a condition that the third signal S3 is high.

In the fourth step, the first signal S1 is synchronized with the low-high transition of the first clock CLK1 to be changed from low to high on a condition that the fed-back fourth signal S4 is high.

In the fifth step, the second signal S2 is synchronized with the low-high transition of the first clock CLK1 to be changed from high to low on a condition that the first signal S1 is high.

In the sixth step, the third signal S3 is synchronized with the low-high transition of the second clock CLK2 to be changed from high to low on a condition that the second signal S2 is low.

In the seventh step, the fourth signal S4 is synchronized with the low-high transition of the second clock CLK2 to be changed from high to low on a condition that the third signal S3 is low.

In the eighth step, the pulse generator 300 receives the third signal S3 and the fourth signal S4 to generate an output signal Output. The generated output signal Output is stably synchronized with the first and second clocks CLK1 and CLK2.

In the ninth step, the first signal S1 is synchronized with the low-high transition of the first clock CLK1 to be changed from high to low on a condition that the first signal S1 is high.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A synchronizing circuit comprising:
  an input signal synchronized with a transition of a first clock;
  an input device for generating a first signal in response to the input signal, for storing the first signal to be synchronized with a transition of a second clock by feeding back the first signal to the input device, and for initializing the first signal in response to a second signal;
  a first device for generating a third signal in synchronization with the transition of the second clock in response to the first signal;
  a second device for generating the second signal in synchronization with the transition of the second clock in response to the third signal; and
  a pulse generator for generating an output signal in response to the second and third signals,
  wherein the input device comprises:

an input signal processor for generating a set signal in response to the input signal, for generating a reset signal in response to the second signal, and for generating a maintenance signal in response to the first signal fed-back to the input signal processor; and a third device for generating the first signal in synchronization with the transition of the first clock in response to the set signal, for storing the first signal so that the first signal is synchronized with the transition of the second clock in response to the maintenance signal, and for initializing the first signal in synchronization with the transition of the first clock in response to the reset signal.

2. The synchronizing circuit as set forth in claim 1, wherein the first clock has a higher frequency than the second clock.

3. The synchronizing circuit as set forth in claim 1, wherein the input signal processor comprises:

a first multiplexer for selecting data "0" according to the second signal to generate the reset signal; and a second multiplexer for selecting data "1" according to the input signal to generate the set signal.

4. The synchronizing circuit as set forth in claim 3, wherein the input signal processor generates the set signal when the input signal and the second signal are inputted simultaneously.

5. The synchronizing circuit as set forth in claim 3, wherein the input signal processor receives the fed-back first signal to generate the maintenance signal when the input signal and the second signal are not inputted.

6. A synchronizing circuit comprising:

an input signal synchronized with a transition of a first clock;

a first device for generating a second signal in response to a first signal fed-back to the first device in synchronization with a transition of the first clock and for outputting the second signal;

an input device for generating a third signal in response to the input signal, for storing the third signal to be synchronized with a transition of a second clock by feeding back the third signal to the input device, and for initializing the third signal in response to the second signal;

a second device for generating a fourth signal in synchronization with the transition of the second clock in response to the third signal;

a third device for generating the first signal in synchronization with the transition of the second clock in response to the fourth signal; and a pulse generator for generating an output signal in response to the first and fourth signals, wherein the input device comprises:

an input signal processor for generating a set signal in response to the input signal, for generating a reset signal in response to the second signal, and for generating a maintenance signal in response to the third signal fed-back to the input signal processor; and a fourth device for generating the third signal in synchronization with the transition of the first clock in response to the set signal, for storing the third signal so that the third signal is synchronized with the transition of the second clock in response to the maintenance signal, and for initializing the second signal in synchronization with the transition of the first clock in response to the reset signal.

7. The synchronizing circuit as set forth in claim 6, wherein the first clock has a higher frequency than the second clock.

8. The synchronizing circuit as set forth in claim 6, wherein the input signal processor comprises:

a first multiplexer for selecting data "0" according to the second signal to generate the reset signal; and a second multiplexer for selecting data "1" according to the input signal to generate the set signal.

9. The synchronizing circuit as set forth in claim 8, wherein the input signal processor generates the set signal when the input signal and the second signal are inputted simultaneously.

10. The synchronizing circuit as set forth in claim 8, wherein the input signal processor generates the maintenance signal in response to the third signal fed-back to the input signal processor when the input signal and the second signal are not inputted.

11. The synchronizing circuit as set forth in claim 6, wherein the first, second, third and fourth devices are flip-flops.

12. A synchronizing circuit comprising:

an input signal synchronized with a transition of a first clock;

a plurality of first flip-flops for generating a second signal in response to a first signal fed-back to the plurality of first flip-flops in synchronization with a transition of the first clock, wherein at least two of the plurality of first flip-flops are connected in series;

an input device for generating a third signal in response to the input signal, for storing the third signal to be synchronized with a transition of a second clock by feeding back the third signal to the input device, and for initializing the third signal in response to the second signal;

a second flip-flop for generating a fourth signal in synchronization with the transition of the second clock in response to the third signal;

a plurality of third flip-flops for generating the first signal in synchronization with the transition of the second clock in response to the fourth signal, wherein at least two of the plurality of third flip-flops are connected in series; and a pulse generator for generating an output signal in response to the fourth signal, and the first signal generated by at least one of the plurality of third flip-flops, wherein the input device comprises:

an input signal processor for generating a set signal in response to the input signal, for generating the reset signal in response to the second signal, and for generating a maintenance signal in response to the Third signal fed-back to the input signal processor; and a fourth flip-flop for generating the third signal in synchronization with the transition of the first clock in response to the set signal for storing, the third signal so that the third signal is synchronized with the transition of the second clock in response to the maintenance signal, and for initializing the third signal in synchronization with the transition of the first clock in response to the reset signal.

13. The synchronizing circuit as set forth in claim 12, wherein the first clock has a higher frequency than the second clock.

14. The synchronizing circuit as set forth in claim 12, wherein the input signal processor:

a first multiplexer for selecting data "0" according to the second signal to generate the reset signal; and a second multiplexer for selecting data "1" according to the input signal to generate the set signal.

15. The synchronizing circuit as set forth in claim 14, wherein the input signal processor generates the set signal when the input signal and the second signal are inputted simultaneously.

16. The synchronizing circuit as set forth in claim 14, wherein the input signal processor generates the maintenance signal in response to the third signal fed-back to the input signal processor when the input signal and the second signal are not inputted.

17. The synchronizing circuit as set forth in claim 12, wherein the first, second, third and fourth flip-flops are D-flip-flops.

* * * * *